United States Patent [19]

Greissinger et al.

[11] Patent Number: 5,279,832
[45] Date of Patent: Jan. 18, 1994

[54] ACTIVE-SUBSTANCE PREPARATION FOR ORAL ADMINISTRATION, ESPECIALLY TO RUMINANTS

[75] Inventors: Dieter Greissinger, Bad Homburg; Heidermarie Kniesel, Blankenbach; Winfried Heimbeck, Mömbris; Herbert Tanner, Hanau, all of Fed. Rep. of Germany

[73] Assignee: Degussa AG, Fed. Rep. of Germany

[21] Appl. No.: 820,777

[22] Filed: Jan. 15, 1992

[30] Foreign Application Priority Data

Jan. 15, 1991 [DE] Fed. Rep. of Germany ....... 4100920

[51] Int. Cl.$^5$ .................................................. A61K 9/44
[52] U.S. Cl. ..................... 424/438; 424/464; 424/467; 424/472; 424/474
[58] Field of Search ............. 424/438, 467, 468, 464, 424/474

[56] References Cited

U.S. PATENT DOCUMENTS

| | | | |
|---|---|---|---|
| 2,853,420 | 9/1958 | Lowey | 424/19 |
| 3,119,738 | 1/1964 | Nichols | 424/195 |
| 3,146,169 | 8/1964 | Stephenson et al. | 424/464 |
| 3,166,476 | 1/1965 | Lowey | 424/464 |
| 3,453,360 | 7/1969 | Hill | 424/465 |
| 3,880,990 | 4/1975 | Bauer et al. | 424/19 |
| 3,927,194 | 12/1975 | Geller | 424/467 |
| 4,353,887 | 10/1982 | Hess | 424/467 |
| 4,717,567 | 1/1988 | Wu et al. | 424/438 |
| 4,824,677 | 4/1989 | Shah | 424/467 |
| 4,832,967 | 5/1989 | Autant et al. | 424/438 |
| 4,837,004 | 6/1989 | Wu | 424/438 |
| 4,876,096 | 10/1989 | Autant | 424/438 |
| 4,877,621 | 10/1989 | Ardaillon | 424/438 |
| 5,009,896 | 4/1991 | Becker | 424/467 |
| 5,061,494 | 10/1991 | Ni | 424/467 |

FOREIGN PATENT DOCUMENTS

0236002 2/1987 European Pat. Off.
760403 10/1952 United Kingdom.
2020181 5/1979 United Kingdom.

*Primary Examiner*—Thurman K. Page
*Assistant Examiner*—Raj Bawa
*Attorney, Agent, or Firm*—Cushman, Darby & Cushman

[57] ABSTRACT

A dosage form for administering physiologically active substances to animals, especially ruminant animals. The dosage unit includes a core which contains the active substance and a coating. The coating has selected areas which are thinner than the average thickness of the coating and/or areas which are predetermined rupture sites. These thin areas or predetermined rupture sites are constructed and arranged so as to detach and/or rupture under the conditions which are present after oral administration of the dosage form. As a result, the delayed release of the physiologically-active substance is accelerated. For example, the coating may be formulated to not be affected in the first stomach of a ruminant but to rapidly disintegrate in the animal's second stomach.

35 Claims, 1 Drawing Sheet

ACTIVE-SUBSTANCE PREPARATION FOR ORAL ADMINISTRATION, ESPECIALLY TO RUMINANTS

The present invention relates to a dosage form containing a biologically-active substance and formulated for oral administration, especially to ruminants. The dosage form contains an active-substance core comprising at least one biologically active substance and having a coating surrounding this core which coating effects a delayed release of the core after oral administration. The invention also relates to the use of this dosage form for the nourishment or veterinary care of ruminants and to a method for supplying ruminants with active substances.

BACKGROUND OF THE INVENTION

Frequently, additional biologically-active substances must be administered to animals raised and kept for the production of e.g. meat, milk, wool or eggs, e.g. for supplying them with amino acids supplements, vitamins or veterinarily active substances. This generally poses no problems in the case of monogastric animals because the active substances to be supplied to them can be quite simply administered orally, e.g. mixed into the feed as an additive or in the form of gelatin capsules containing the active substance. However, such simple methods generally fail in the case of ruminants because the active substances to be supplied are metabolized at least for the most part in the rumen by the rumen flora and, in any case, are available in a low amount for direct resorption in the following intestinal tract. If a delayed release of the active substance is desired in addition thereto, this poses problems even in monogastric animals, especially when a large dose must be administered, since the active substance is generally either bound to a matrix or is embedded in a matrix and the matrix can usually contain only a small amount of the active substance. Also, diffusion-controlled release of active substances is difficult to coordinate and is hardly suitable for administering large amounts of active substance. Also to be considered is the cost of preparing the dosage forms.

An almost limitless number of suggestions have already been made for solving these problems. They all have in common the fact that the active substance to be supplied is protected against premature release in the rumen or the stomach by embedding it in a matrix or by surrounding it with a coating. A variety of materials can be used for the matrix or the coating. However, none of the known suggested solutions is completely satisfactory because substances must be used as component for the protective materials which are either not legally acceptable for ruminant nutrition or at least not yet or are not readily available, require an expensive pretreatment or the particles prepared with their help tend to adhere during storage and/or are thermally and mechanically not sufficiently stable.

SUMMARY OF THE INVENTION

The object of the present invention is to make available an active-substance preparation which offers a slow-release effect with a broad protection of the active substance in the rumen or the stomach but releases the active substance in the ensuing intestinal tract, which can be produced in a simple and economic manner from as few substances as possible, which are physiologically completely compatible and which are thermally and mechanically stable. Further objects of the invention are to provide for the use of such a preparation to supply ruminants with the active substance.

These and other objects are achieved in a dosage form in which the active substance is enclosed in a coating which has rather thin areas and/or predetermined rupture sites which accelerate the delayed release vis-à-vis an essentially uniform coating.

The term "rupture sites" denotes such areas which result in the separation of entire coating parts as such or in the breaking apart of the active-substance preparation. This can occur e.g. in that an essentially capsule-shaped active-substance preparation breaks apart in the middle or that one or several coverings e.g. of a pellet peel off. The predetermined rupture sites are usually tapered areas or thinner areas, preferably in the form of an annulus. The encasing coating should consist of a material which is not oily but rather preferably brittle at the body temperature of the mammal to which the active-substance preparation is administered. An oily casing would re-cover the predetermined rupture sites in the coating as a consequence of the stomach or intestinal activity, so that the desired effect can not occur. Likewise, coatings which are soft or too elastic are poorly suited for the purposes of the invention, since they break open and release the active substance only with difficulty on account of their shock-absorbing property. On the other hand, the casing should be so stable that the active-substance preparation does not break apart during normal handling. This can also be achieved e.g. in that the active-substance core is not a loose powder but rather is a unitary object, so that minor damage to the coating even prior to oral administration is harmless and no active substance is lost before the administration as a result of damage and only a small opening remains after the oral administration from which the active substance is dissolved only slowly. A sufficient delay of the release of the active substance is also achieved.

The coating is generally built up from a film former. Naturally occurring or modified naturally occurring polymers or homo- and copolymers which can be produced according to customary known methods can be used as film formers. Such suitable polymers are e.g. cellulose esters, cellulose ethers, cellulose acrylates, poly(meth)acrylates, polyamides, polyesters and copolymers of e.g. acrylonitrile, an optionally substituted vinyl pyridine with e.g. styrene, ethylene, propylene, butadiene or esters and amides of methacrylic acid or acrylic acid. A softener such as, e.g., diethylphthalate, polyethylene glycol or a citric-acid ester or further adjuvants such as silica, talcum or alkali stearates or alkaline-earth stearates can optionally be added to the film former. The coating should be selected in such a manner that a peeling off which is not too rapid takes place. According to the invention, film formers can be used which do not permit any or only a very slight (<50%) release of the active substance with a uniform coating but the desired action takes place nevertheless through the predetermined rupture sites.

A coating based on a cellulose ether, preferably ethyl cellulose and in particular such a coating with an additional, inner, filled layer is quite particularly suitable.

The coating is preferably 1.5 to 30% by weight, relative to the weight of the active-substance core. It is advantageous in this instance if the film former is present, again in relation to the weight of the active-substance core, at 1 to 20% by weight and the adjuvant or filler at 0.5 to 10% by weight; a combination of both is the most favorable. The ratio between film former and filler should normally be in the range of 10:1 to 1:5 and a ratio between 5:1 to 1:2 is preferred.

Suitable fillers are especially metal carbonates, silicas, silicates, alginates, stearates, starches and rubbers. Such suitable fillers are e.g. magnesium-, calcium or sodium carbonate, precipitation silica, calcium-, aluminum- or sodium aluminum silicate, calcium-, sodium or aluminum alginate, sodium stearate, corn starch or gum arabic or a mixture of two or more of these substances. The particle size of the fillers is of little importance. The size should be, if possible, distinctly smaller than the layer thickness and is customarily in a range of 0.1-30 μm, preferably 0.7-10 μm.

Especially suitable coatings contain two layers, an inner one consisting of the total amount of the filler and 0.2 to 8% by weight film former, again in relation to the weight of the active-substance core, and an outer layer containing the remainder of preferably the same film former.

Such a coating is sufficiently brittle, so that it breaks up gradually after the oral administration, as a result of which the active substance is released gradually in a delayed fashion. The double coating based on a cellulose ether is also suitable for breaking up and releasing the active substance without the described predetermined rupture sites. Other favorable points, in this connection, are also the simple manufacture, the low material cost and the legal acceptability in accordance with nutrition and feed laws. The combination of this coating with the predetermined rupture sites which aid the break-up is especially advantageous.

The thinner areas, which can also be present in a continuous fashion as an area which is e.g. areal or preferably in the form of closed lines, especially circular lines, advantageously extend over at least 0.5% (areal percent) of the entire surface of the coating and as a rule more than at least 1%. Thin areas are especially suitable which constitute at least 2% of the entire surface of the coating and especially in the case of areal instead of linear thinner areas their area is approximately at least 5% of the entire surface. Normally, the areas of the thinner areas should not exceed 20% of the entire surface of the coating; particularly in the case of linear thinner areas, 10% of the entire surface is generally not exceeded. The thinner area should be at least 20% below the average layer thickness; at least 30% is preferable and especially at least 50%. On the other hand, the thinner area should not be too thin, as otherwise a break can occur too rapidly. It is generally advantageous if at least 10% of the average layer thickness is maintained. Basically, small-area, thinner areas in the layer thickness should be especially thin in order to reliably break open.

The thinner areas and/or predetermined rupture sites are preferably formed by edges. Such edges occur e.g. in pellets or tablets and the thinner areas and/or predetermined rupture sites are readily achieved in that the edges are not dulled before the coating but rather remain as sharp edges. The coating then takes place on the areas thicker than on the edge. Likewise, the entire coating must not be applied in too thick a manner as otherwise the release of the active-substance core will take place too slowly or not at all in spite of the formed thinner areas. 5 to 150 μm, especially 10 to 80 μm and especially preferably 20 to 60 μm were found to be the favorable average layer thicknesses. If the thinner areas and/or predetermined rupture sites are formed by edges, the adjacent areas forming the edges preferably form an angle of $\leq 120°$, preferably $\leq 90°$ and especially $\leq 70°$. An angle below 20° should not be used and angles above 45° are preferred. The areas adjoining the edge are preferably not too small, that is, they should have a length vertical to the edge of at least 0.05 mm, preferably at least 0.1 mm and especially at least 0.2 mm. It is advantageous if the edges do not exhibit too great a radius, that is, they should be sufficiently sharp-edged. An edge radius of $\leq 1$ mm, preferably $\leq 0.7$ mm and especially $\leq 0.5$ mm is suitable. It is especially advantageous in this connection if the radius of the edge exhibits at the most the length of the areas adjacent to the edge vertical to the edge; in particular, the radius should be at the most ⅔ and in an especially favorable manner at the most one half of this length. Such edges, especially those with a very small radius, are sufficiently susceptible to mechanical actions and are especially thinly coated, so that the coating breaks open at these edges and the active substance is gradually released.

The successive release of the active substance should be regulated in such a manner for ruminants by the selection of the coating and the design of the coating that 6 hours ($\approx$ the average dwell time in the rumen) after oral administration, at the most 50%, preferably at the most 30% and especially at the most 20% has been released. On the other hand, after 24 hours after oral administration, at least 50% by weight, preferably at least 70% by weight and especially at least 80% by weight of the biologically active substance should have been released. It is advantageous if a part of the active substances had been released, even before 6 hours, since this serves e.g. to nourish rumen bacteria As a rule, a release of at least 2% by weight, preferably 5% by weight and especially 10% by weight of the biologically active substance is achieved with the coatings of the invention after 6 hours after the oral administration. In this respect, the coating of the invention is clearly superior to purely pH-dependent coatings since the latter generally release no active substance at all in the rumen and on the other hand they bring about a sudden release of the active substance. For applications other than in ruminants, the release of the active substance is generally adjusted in such a manner that after 2 hours after the oral ingestion, at the most 50% by weight, preferably at the most 30% by weight and especially at the most 20% by weight has been released. Then, after 8 hours, at least 40% by weight, preferably at least 50% by weight and especially preferably at least 75% by weight should have been released. Such values permit an essentially uniform supplying of the organism with the active substance with only two administrations per day. The preparations provided with the thinner areas and/or predetermined rupture sites of the invention generally deliver at least 20% more active substance thereby after the above-cited times than the preparations with an essentially uniformly thick coating, usually even more than 30 and in special instances more than 50% by weight is released.

The coating of the invention has the advantage that its properties can be adjusted in such a manner in accordance with its composition and/or design that the release of the active substance takes place largely independently of the pH of the particular medium or of the presence of enzymes or other breakdown-promoting substances entirely or partially in the areas of the gastrointestinal tract in which the availability of the active substance is desired. For example, it can be arranged that a slight part of the active substance is released in the rumen, as is desirable e.g. in the case of nicotinamide, and/or that the main amount of the active substance is available rapidly, or in a few instances with slow-release effect, in the small intestine, the actual resorption site for the active substance.

It is especially important that cellulose ether and the fillers have previously been used for a long time with success in animal feeding and are accepted without limitation by feed laws.

The designations, "active substance" and "biologically-active substance", as used herein, refer to animal feeds, nutrients and drugs [veterinary-active medications]. These include for example, proteins, amino acids and amino-acid derivatives, vitamins, carbohydrates, hormones and other (animal) medications. Examples of proteins are e.g. feather meal, fish meal, casein or potato protein; of amino acids and amino-acid derivatives: Methionine, lysine, threonine, tryptophane, N-acyl amino acids, hydroxy amino acids or their physiologically compatible (metal) salts or peptides; of vitamins: Vitamin A, vitamin A acetate, vitamin D, vitamin E, nicotinic acid or nicotinic-acid amide, the B vitamins or choline chloride; of carbohydrates: glucose, starch or saccharose; of hormones and (animal) drugs: estrogen, thyrotropin, antibiotics, anthelmintics or paraciticides. Of course, combinations of several such active substances can also be used.

The active substance or the active-substance combination is advantageously formed with a binder into pellets tablets or granulates and compressed using conventional compaction methods such as extrusion, tabletting, spray-, fluid-bed- or agitated granulation. The binder can be substances such as non-toxic rubbers, starch, gelatins, cellulose derivatives, alginates and similar known substances which are customarily used in food or fodder processing as binding, gelling, thickening or tabletting agents.

Other substances such as silicas, silicates, metal carbonates, metal phosphates or metal oxides and alkali-metal stearates can optionally be used as auxiliary flux agents, as lubricants, density regulators or adsorbents for liquid active substances.

The active-substance cores produced in this manner are subsequently encased in such a manner with the protective coating that they are brought into contact with a solution of the film former in which the filler is optionally suspended and the solvent is then evaporated. Suitable solvents can be found among the hydrocarbons, short-chain alcohols or ketones and are e.g. toluene, isopropyl alcohol, methanol, ethanol, acetone or mixtures of such solvents.

The film former, which is soluble therein, is advantageously a cellulose ether which is advantageously insoluble or slightly soluble in water or is a mixture of several such cellulose ethers, but preferably ethyl cellulose.

The filler is selected with advantage from the above-mentioned substances. Of course, mixtures of such fillers can also be used. The filler has several advantageous effects: On the one hand, it renders the film former brittle, thus facilitating the breaking up of the coating; on the other hand, it acts like a sponge for the gastric juices (or other juices), which facilitates the breaking off or opening up of the coating, and finally, the filler layer permits the application of a thinner outer layer so that in particular the mechanical peeling off of the coating described above is facilitated. A coating with a high filler content through the entire coating is usually not suitable since the coating disintegrates too rapidly.

The known and customary methods, e.g. various fluid-bed and coating methods are suitable as coating method.

The production of the active-substance preparation in accordance with the invention takes place in a typical instance in such a manner that the active, substance is mixed with 5 to 95% by weight, preferably 10 to 20% by weight, relative to the weight of the active substance, of the binder or of a mixture of the binder and water or a saturated solution of the active substance in water and is pressed to tablets or pellets, or that the active substance is granulated together with the binder. The tablets or pellets should preferably be 0.5 to 2 mm $\times$ 1 to 5 mm and the (angular) granulates 1 to 2 mm in size; however, they can also be larger or smaller. Pellets and tablets are especially preferred for this coating since the thin areas or predetermined rupture sites are also obtained with them in a simple manner.

After drying, the active-substance cores produced in this manner are first sprayed with the suspension of the filler in a solution of the film former and then with the pure solution of the film former. The coating constitutes 1.5 to 30% by weight, preferably 2.5 to 20% by weight and especially 4 to 14% by weight, relative to the weight of the active-substance core, and contains, again in relation to the weight of the active-substance core, 1 to 20% by weight, preferably 2 to 15% by weight and especially 3 to 10% by weight film former and 0.5 to 10% by weight, preferably 0.5 to 5% by weight and especially 1 to 4% by weight filler.

The coating is generally applied in such a manner that a 2 to 20% by weight, preferably 4 to 15% by weight solution of the film former is prepared in a suitable solvent or solvent mixture and is sprayed on in isolated and sequential steps in such a manner that the inner layer contains, again in relation to the weight of the active-substance core, 0.2 to 8% by weight, preferably 0.2 to 5% by weight and especially 0.5 to 3.5% by weight film former and the entire amount of filler. After the evaporation of the solvent or solvents from this first layer, the remainder of the filmformer solution is sprayed on in order to form a second layer and the solvent or solvents is (are) again evaporated.

If angular active-substance cores such as e.g. pellets or tablets are coated in this manner, then a coating is obtained which is distinctly thinner on the edges. The particle can then break open in the stomach or the intestine at these "weak points", even if film formers such as e.g. cellulose ether, which is partially on top, are used which are only slightly soluble or even non-soluble in the digestive juices. The coating process should naturally take place with caution so that the edges are not rounded off too much.

REFERENCE TESTS

The invention will be illustrated in more detail in the following examples and reference tests. All percent data indicates % by weight.

In order to estimate the protective action of the coating, an in-vitro test can be as a reference which simulates the conditions in the digestive system e.g. of a ruminant at least as regards the pH, the temperature and partially also the motion. To this end, the active-substance preparation produced is incubated in a shaking water bath at 37° C. in three different buffer solutions, one after the other, first for 6 hours in a citrate buffer produced by dissolving 72 g citric acid×1 H₂O and 19.5 g NaOH in water and diluting with water to 1 liter with a pH of 5.5; then for 2 hours in an HCl/KCl buffer produced by diluting 250 ml 0.2M KCl solution and 65 ml 0.2M HCl solution with water to 1 liter with a pH of 2.0; and finally for 16 hours in a citrate buffer produced by dissolving 42 g citric acid×1 H₂O and 23 g NaOH in water and diluting with water to 1 liter with a pH of 6.5. Depending on the time indicated, the undissolved component of the active substance in the particles is determined by HPLC and indicated relative to the 100 percent content before the test in the form a % after the incubation at pH 5.5./b % after the incubation at pH 2.0/c % after the incubation at pH 6.5.

It was found that the values obtained in this manner correlate well with results from in-vivo tests and yield a rapid and reliable estimate of the suitability of the tested particles, thereby reducing the need for in vivo testing.

BRIEF DESCRIPTION OF FIGURE OF DRAWING

The invention will be described in more detail by reference to the drawing in which.

DETAILED DESCRIPTION OF THE PREFERRED EMBODIMENTS

Figure 2:
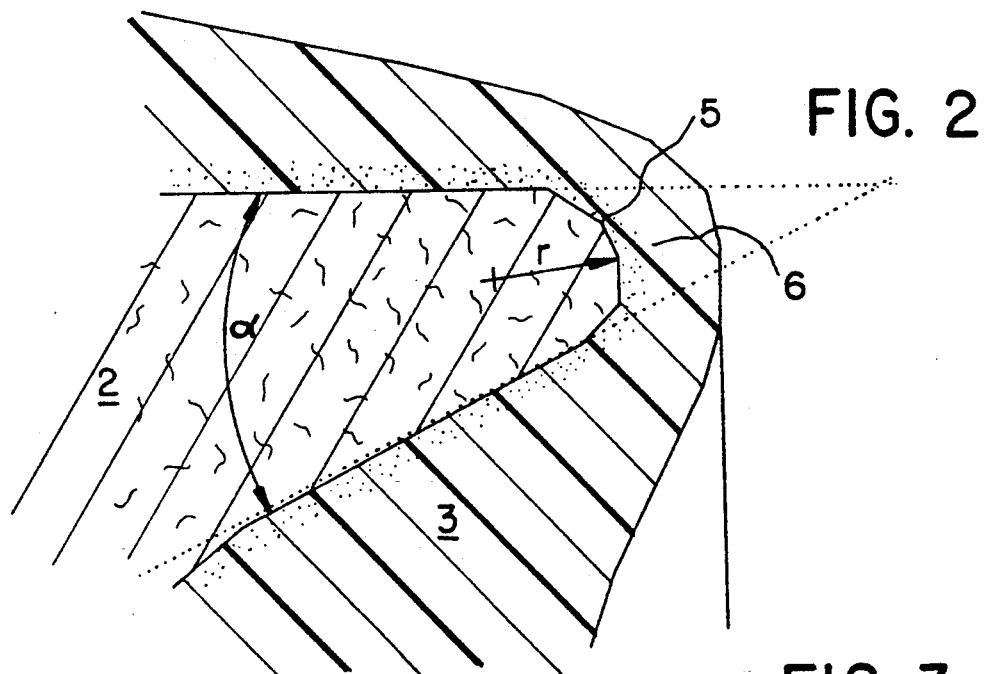
FIG. 2 is an enlarged view of a portion of FIG. 1 marked by broken lines.

The surface of a pellet 1 with an active substance core 2 is completely covered by a coating 3. The coating 3 may include a filler 11, which is preferably in the inner layer near the active substance core 2. The end walls 4 of the pellet are concave, thus forming two circular edges 5 with the angle α (dotted lines in FIG. 2). In the area of these edges 5, the coating 3 is considerably thinner than in the other areas of the pellet 1, so that a predetermined rupture site 6 is formed. The formation of the predetermined rupture site 6 and the breaking open of said site is favored by the edges 5 which form an acute angle α with their adjacent areas (i.e., in the given example, the curved surface 7 and the corresponding end wall 4 of the pellet 1).

The angle α is determined by the curved surface 7 and the tangent of the end wall 4 to the edge 5.

Likewise, the radius r of the edge 5 and the length L of the areas 7 and 4 adjacent to the edge 5 (measured perpendicularly to the edge 5) are responsible for the function, that is the breaking open of the predetermined rupture site 6. The length L is measured up to the next considerable change of the corresponding area, i.e., for the given example in the case of the curved surface 7 up to the other edge and in the case of the end wall 4 up to the opposite part of the corresponding circular edge 4. If these lengths L are too small, the predetermined rupture site will be especially thickly coated, so that the desired effect cannot occur.

Figure 1:
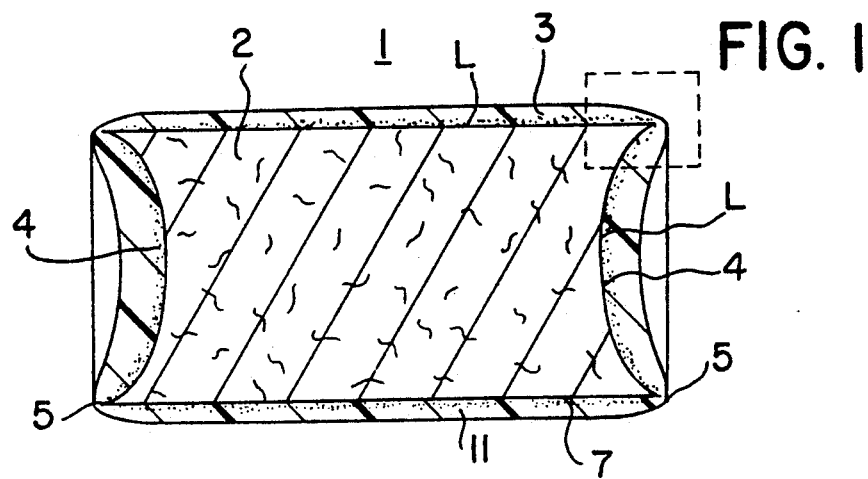
FIG. 1 is an elevation view, in cross-section, along the longitudinal axis of a pellet coated according to the invention.
Figure 3:
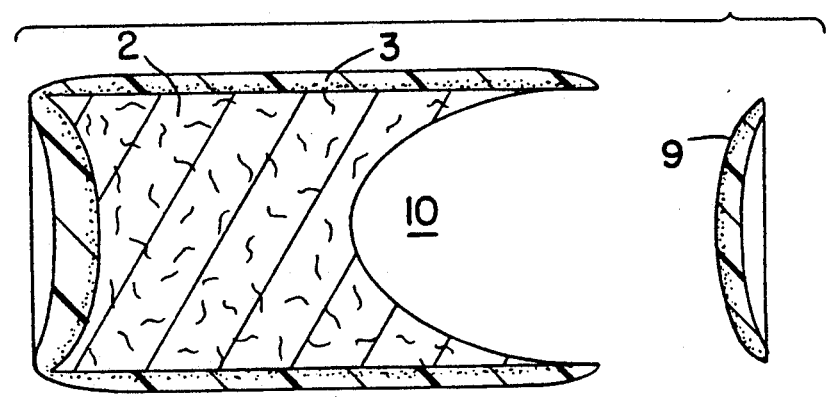
FIG. 3 is a view of the pellet of FIG. 1 with one circular edge broken open.

FIG. 3 shows the pellet of FIG. 1 where the endwall is broken open. At the end wall 4, the coating 3 is broken open like a lid my mechanical action or by partial dissolution of the coating 3 in the area of the predetermined rupture site 6, so that the active substance is released from the core in the area 10.

The following examples illustrate the invention.

EXAMPLE 1

3,600 g DL-methionine and 400 g of the sodium salt of carboxymethylcellulose are placed in a receiver and combined with intensive mixing with 870 g water. The mixture is pressed in an annular grind-and-mix press with 1.5 mm matrix bore to pellets which are cut to a length of approximately 2 mm and dried at 60° C.

100 g of these pellets are sprayed in a coating device, at first with a solution of 0.5 g ethyl cellulose in 25 ml ethanol in which 2.5 g sodium aluminum silicate (particle size 3.5 μm) are suspended. Then, a solution of 3.5 g ethyl cellulose in 95 ml ethanol is sprayed on. The particles coated in this manner are dried under reduced pressure at 60° C. Their methionine content, determined by bromatometric titration, is 83.6% and the undissolved portion of the methionine 75% /63% /18%.

EXAMPLE 2

100 g of the pellets produced according to Example 1 are coated as in Example 1 using a total of 4 g ethyl cellulose (inside 1 g, outside 3 g) and 1.5 g sodium aluminum silicate. The methionine content is 84.6% and the particular undissolved portion of the methionine 70% /56%/13 %.

EXAMPLE 3

100 g of the pellets produced according to Example 1 are coated as in Example 1 using a total of 5 g ethyl cellulose (inside 1.25 g, outside 3.75 g) and 2.5 g sodium aluminum silicate. The methionine content is 83.0 % and the particular undissolved portion of the methionine 77%/64%/21%.

EXAMPLE 4

100 g of the pellets produced according to Example 1 are coated as in Example 1 using a total of 8 g ethyl cellulose (inside 2 g, outside 6 g) and 5 g sodium aluminum silicate. The methionine content is 79.5% and the particular undissolved portion of the methionine 93%/87%/47%.

REFERENCE EXAMPLE 5

The pellets produced according to Example 1 are treated in such a manner in a customary apparatus suitable for this purpose, e.g. in a rounding device, that the edges and webs of the invention are ground off to a large extent. Then, 100 g of the pellets rounded in this manner are coated as in Example 1 using a total of 4 g ethyl cellulose (inside 0.5 g, outside 3.5 g) and 2 g sodium aluminum silicate. The methionine content is 84.8% and the undissolved portion of the methionine 94%/91%/74%.

This reference test shows that after the edges and webs have been ground off, thus eliminating predetermined rupture sites, by far the greatest part of the methionine still remains undissolved even after 24 hours.

EXAMPLE 6

100 g of the pellets produced according to Example 1 are coated as in Example 1 using a total of 5 g ethyl cellulose (inside 1.25 g, outside 3.75 g) and 2.5 g ammonium alginate as filler. The methionine content is 84.1% and the undissolved portion of the methionine 86%/76%/34%.

EXAMPLE 7

100 g of the pellets produced according to Example 1 are coated as in Example 1 using a total of 5 g ethyl cellulose (inside 1.25 g, outside 3.75 g) and 2.5 g magnesium carbonate as filler. The methionine content is 83.4% and the undissolved portion of the methionine 91%/82%/43%.

EXAMPLE 8

100 g of the pellets produced according to Example 1 are coated as in Example 1 using a total of 5 g ethyl cellulose (inside 1.25 g, outside 3.75 g) and 2.5 g starch as filler. The methionine content is 83.4% and the undissolved portion of the methionine 84%/75%/31%.

EXAMPLE 9

100 g of the pellets produced according to Example 1 are coated as in Example 1 using a total of 5 g ethyl cellulose (inside 1.25 g, outside 3.75 g) and 2.5 g gum arabic as filler. The methionine content is 83.8% and the undissolved portion of the methionine 91%/83%/40%.

EXAMPLE 10

100 g of the pellets produced according to Example 1 are coated as in Example 1 using a total of 5 g ethyl cellulose (inside 1.25 g, outside 3.75 g) and 2.5 g sodium stearate as filler. The methionine content is 82.9% and the undissolved portion of the methionine 78%/65%/18%.

EXAMPLE 11

The same method is used as in Example 1, but 400 g starch are used instead of the sodium salt of carboxymethylcellulose in the production of the active-substance pellets. 100 g of these pellets are coated as in Example 1 using a total of 5 g ethyl cellulose (inside 1.25 g, outside 3.75 g) and 2.5 g sodium aluminum silicate as filler. The methionine content is 84.2% and the undissolved portion of the methionine 80%/69%/29%.

EXAMPLE 12

The same method is used as in Example 1, but 360 g starch and 40 g sodium stearate are used instead of the sodium salt of carboxymethylcellulose in the production of the active-substance pellet.

100 g of these pellets are coated using a total of 3.5 g ethyl cellulose (inside 1 g, outside 2.5 g) and 2 g sodium aluminum silicate as filler. The methionine content is 85.5% and the undissolved portion of the methionine 66%/54%/8%.

EXAMPLE 13

100 g of the pellets produced according to Example 12 are coated using a total of 4 g ethyl cellulose (inside 1 g, outside 3 g) and 2 g sodium stearate as filler. The methionine content is 84.8% and the undissolved portion of the methionine 73%/63%/19%.

REFERENCE EXAMPLE 14

100 g of the pellets produced according to Example 1 are coated in only one layer with a solution of 7.5 g ethyl cellulose in 200 ml ethanol without using a filler. The methionine content is 83.4% and the particular undissolved portion of methionine 88%/81%/54%.

This reference test shows that, given a relatively thick and elastic coating of the active-substance core in one layer, the greatest part of the methionine remains undissolved even after a total of 24 hours.

EXAMPLE 15

100 g of the pellets produced according to Example 1 are coated in only 1 layer with a solution of 5 g ethyl cellulose in 400 ml ethanol in which 2.5 g sodium aluminum silicate are suspended. The methionine content is 83.1% and the particular undissolved portion of the methionine 36%/19%/0%.

This test shows in comparison to Example 3 that the coating with the same amount of ethyl cellulose and sodium aluminum silicate but in only one layer protects the methionine only to an insufficient extent from dissolution already under the conditions in the rumen.

On the other hand, this coating is suitable for non-ruminants since only 81% of the active substance has been released after 8 hours. The slow-release effect obtained brings about a uniform supplying of the organism with the active substance in 2 doses/day.

ANIMAL TESTS

The following investigations using animal tests demonstrate the superior action of the product of the invention. The rise of the methionine content in the blood plasma of milk cows was examined. Since all nutrients contained in milk and their precursors are supplied to the mammary gland with the blood stream, the methionine from a protected product must arrive there in the blood.

PRELIMINARY TEST

The extent of the rise of methionine in the blood plasma upon administration of defined amounts of protected methionine is tested in preliminary examinations in which methionine preparations are introduced directly into the abomasum after 6 hours pre-incubation in the rumen (simulation of the natural dwell time).

The product to be tested was sewn in portions of 25 g into nylon bags (30 μm pore size) and pre-incubated for 6 hours in the rumen of the test cows (3 animals) (max. 6–8 bags per animal). After having been removed, the bags were cleaned of fodder particles but not washed. The contents of all bags were pooled and weighed to determine the substance loss. The methionine content was determined in a specimen of the pre-incubated, pooled material, from which the methionine amount which disappeared during the 6 hours can be calculated at 17% by weight and the amount of rumen-stable methionine at 83% by weight. A known product which was also tested (reference Example 17) was 100% stable in the rumen.

The pre-incubated material was then weighed into gelatin capsules which dissolve within a few minutes in the abomasum. The administration took place four times daily in the 3 animals through the rumen fistula directly into the abomasum. 25 g methionine per day was administered in this manner over a period of four days (day 1–4).

Day 0 served for obtaining the control parameters. On days 0, 3 and 4 blood samples were taken from the animals by means of puncturing the Vena jugularis at 1 P.M. and 4 P.M. The content of free methionine in the rumen was determined in these samples. There was a rise of the plasma methionine level of approximately 100% in the middle of days 3 and 4 in comparison to day 0.

EXAMPLE 16 AND REFERENCE EXAMPLE 17

In the test, the animals received (4 per product) 30.6 g DL-methionine in the form of pellets produced according to Example 12 which were coated using a total of 4% by weight ethyl cellulose relative to the weight of the active-substance core (inside 0.5%, outside 3.5%) and using 2% by weight sodium aluminum silicate as filler (Example 16) and received 25 g in the form of active-substance granulates which contain 50% by weight DL-methionine and obtain their protection from a coating with monocarboxylic acids with 14–22 atoms (reference Example 17). The animals received the above in a complete ration which consisted of 10% hay, 30% grass silage, 20% corn silage (together 15 kg dry mass/day) and 40% of a grain/coarse soya bean meal feed concentrate (6 kg dry mass/day).

Such products are known from European patent EP 0 037 478 and German DE patent 22 12 568 and are commercially obtainable.

The amounts were calculated in such a manner that, based on the rumen stability of the products measured in the preliminary test, approximately 25 g DL-MET should pass into the small intestine (83% stability for Example 16 and 100% for reference 17). The preparations were administered for 12 days (day 1–12). On days 0, 10, 12 and 14, blood samples were taken (Vena jugularis, 11.50 A.M. and 2.50 P.M.). The table shows the results of the measurements.

The methionine content rises in the blood plasma in both instances. The rise in Example 16 with 188% on day 10 is distinctly higher in comparison to reference 17 with 28%. On day 12, the last day of the oral administration, the corresponding values are +151% and +5%. Two days after discontinuation, the methionine content in the blood plasma has fallen back again to the starting level and in the reference treatment it is even 10% below the starting value.

The differences in the methionine content in the manure correspond to these findings. Whereas in the middle of days 10 and 12 0.074% methionine was found in the manure of the four cows in Example 16, 0.246% was found in reference 17.

| | The Influence of Protected Methionine Products on the Plasma Methionine Level of Cows after a Feeding with Feed Concentrate (KF) (average of 4 cows and 2 times of day) | | | | | | | |
|---|---|---|---|---|---|---|---|---|
| daily MET administration via the KF (g) | daily MET (g) in the small intestine (calculated from preliminary test) | Blood MET level (µmole/l) | | | | Rise of the Blood MET-Level (rel. increase in %) | | |
| | | Control Day 0 | two values each Day 10 | Day 12 | No MET Day 14 | Day 10 | Day 12 | Day 14 |
| 30.6 | 25.4 | 8.3 ± 4.0 | 23.8 ± 8.8 | 20.8 ± 6.0 | 8.4 ± 5.8 | 188 | 151 | 1 |
| 25.0 | 25.0 | 13.4 ± 4.2 | 17.2 ± 4.8 | 14.1 ± 5.9 | 12.1 ± 4.5 | 28 | 5 | −10 |

What is claimed is:

1. In a dosage form for oral administration, containing an active-substance core comprising at least one physiologically active substance and having a continuous coating surrounding said core which coating delays the release of the core after oral administration; the improvement in which said coating has thin areas and/or predetermined rupture sites within an otherwise substantially uniform coating, said thin areas and/or rupture sites having a thickness which is at least 20% below the average layer thickness of the coating and the average layer thickness of the coating being in the range of 5 to 150 micrometers, said coating being 1.5 to 30% by weight relative to the weight of the active substance core and said thin areas and said predetermined rupture sites being constructed and arranged so as to detach and/or rupture, under conditions which are present after oral administration of said dosage form, thereby accelerating the delayed release of said physiologically active substance in such manner that, 24 hours after the oral administration, at least 50% by weight of the biologically active substance has been released.

2. A dosage form as set forth in claim 1 in which the biologically active substance is a pharmaceutically active substance or a nutrient.

3. The dosage form set forth in claim 1 in which said thin areas and/or predetermined rupture sites form a line closed in itself.

4. The dosage form set forth in claim 3 in which the line is essentially circular.

5. The dosage form set forth in claim 4 in which at least two such circular lines are provided.

6. The dosage form set forth in claim 1 in which said thin areas and/or rupture sites extend over at least 0.5% of the entire area of the coating.

7. The dosage form set forth in claim 6 in which said thin areas and/or rupture sites constitute at least 2% of the entire area of the coating.

8. The dosage form set forth in claim 1 in which the said thin areas and/or rupture sites have a thickness which is at least 30% thinner than the average layer thickness of the coating.

9. The dosage form set forth in claim 1 or claim 2 in which said thin areas and/or rupture sites are formed by edges.

10. The dosage form set forth in claim 9 in which the edges are located between areas which are at an angle of $\leq 120°$ to each other.

11. The dosage form set forth in claim 10 in which the edges are located between areas which are at an angle of $\leq 90°$ to each other.

12. The dosage form set forth in claim 9 in which the edges are located between areas which are at an angle of $\leq 70°$ to each other.

13. The dosage form set forth in claim 10 in which said areas have a dimension of at least 0.05 mm perpendicular to the edge.

14. The dosage form set forth in claim 10 in which said areas have a dimension of at least 0.1 mm perpendicular to the edge.

15. The dosage form set forth in claim 10 in which said areas have a dimension of at least 0.2 mm perpendicular to the edge.

16. The dosage form set fort in claim 9 in which the edges have a radius of $\leq 1$ mm.

17. The dosage form set fort in claim 9 in which the edges have a radius of $\leq 0.7$ mm.

18. The dosage form set forth in claim 9 in which the edges have a radius of $\leq 0.5$ mm.

19. The dosage form set forth in claim 16 in which the radius has at the most the dimension of the areas bordering the edge perpendicular to the edge.

20. The dosage form set forth in claim 19 in which the radius is at the most ⅔ of the dimension of the areas bordering the edge perpendicular to the edge.

21. The dosage form set forth in claim 19 in which the radius is at the most ½ of the dimension of the areas bordering the edge perpendicular to the edge.

22. The dosage form set forth in claim 1 in which the release of the biologically active substance is regulated in such a manner that 6 hours after oral administration, at the most 50%, has been released.

23. The dosage form set forth in claim 22 in which the release of the biologically active substance is regulated in such a manner that 6 hours after oral administration, at the most 30%, has been released.

24. The dosage form set forth in claim 22 in which the release of the biologically active substance is regulated in such a manner that, 6 hours after oral administration, at the most 20%, has been released.

25. The dosage form set forth in claim 22 in which the release of the biologically active substance is regulated in such a manner that, 6 hours after oral administration, at least 2% by weight, of the biologically active substance has been released.

26. The dosage form set forth in claim 22 in which the release of the biologically active substance is regulated in such a manner that, 6 hours after oral administration, at least 5% by weight, of the biologically active substance has been released.

27. The dosage form set forth in claim 22 in which the release of the biologically active substance is regulated in such a manner that, 6 hours after the oral administration, at least 10% by weight, of the biologically active substance has been released.

28. The dosage form set in claim 1 in which, 24 hours after the oral administration, at least 70% by weight of the biologically active substance has been released.

29. The dosage form set forth in claim 1 in which, 24 hours after the oral administration, at least 80% by weight of the biologically active substance has been released.

30. The dosage form set forth in claim 1 in which said coating contains 1 to 20% by weight, relative to the weight of the active substance core, of a cellulose ether as film former and 0.5 to 10% by weight, relative to the weight of the active-substance core, of at least one filler selected from the group consisting of metal carbonates, silicas, silicates, alginates, stearates, starches and rubbers, the coating consisting of two layers, the inner layer of which, close to the core, contains 0.2 to 8% weight film former, relative to the weight of the active-substance core, and the entire amount of filler, and the outer layer of which contains the remaining amount of the film former.

31. The dosage form set forth in claim 30 in which the film former is ethyl cellulose.

32. The dosage form as set forth in claim 30 in which the filler is selected from the group consisting of magnesium-, calcium- or sodium carbonate, a precipitated silica, calcium-, aluminum- and sodium aluminum silicates, calcium-, sodium and aluminum alginates, sodium stearate, corn starch, gum arabic and mixtures of two or more of these substances.

33. An animal feedstuff comprising the dosage form set forth in claim 1 or claim 2 and an animal feedstuff.

34. A method of supplying a physiologically active substance to a ruminant animal which comprises orally administering to such animal the dosage unit set forth in claim 1.

35. A method as set forth in claim 34 in which the coating is brittle at the body temperature of the ruminant animal to which the dosage unit is administered.

* * * * *